United States Patent [19]
Behringer

[11] Patent Number: 5,873,717
[45] Date of Patent: Feb. 23, 1999

[54] SYSTEM ACTIVATING A DENTAL HANDPIECE AFTER REMOVAL FROM A HOLDER

[75] Inventor: Wolfgang Behringer, Bensheim, Germany

[73] Assignee: Sirona Dental Systems GmbH & Co. KG, Bensheim, Germany

[21] Appl. No.: 12,409

[22] Filed: Jan. 23, 1998

[30] Foreign Application Priority Data

Jan. 28, 1997 [DE] Germany .................. 197 02 996.5

[51] Int. Cl.⁶ ......................................... A61C 1/02
[52] U.S. Cl. .............................. 433/28; 433/98; 433/101
[58] Field of Search ................... 433/28, 77, 78, 433/80, 84, 29, 101, 126, 98

[56] References Cited

U.S. PATENT DOCUMENTS

| | | | |
|---|---|---|---|
| 3,872,593 | 3/1975 | Thornton, Jr. et al. | 433/28 |
| 4,069,587 | 1/1978 | Peralta | 433/28 |
| 4,351,634 | 9/1982 | Rosenfeldt | 433/28 |
| 4,492,574 | 1/1985 | Warrin et al. | 433/81 |
| 4,514,172 | 4/1985 | Behringer | 433/126 |
| 4,681,540 | 7/1987 | Landgraf et al. | 433/126 |
| 4,720,266 | 1/1988 | Leonard et al. | 433/126 |
| 5,185,532 | 2/1993 | Zabsky et al. | 250/455.11 |
| 5,385,468 | 1/1995 | Verderber | 433/28 |
| 5,669,769 | 9/1997 | Disel | 433/29 |

*Primary Examiner*—Gene Mancene
*Assistant Examiner*—Pedro Philogene
*Attorney, Agent, or Firm*—Hill & Simpson

[57] ABSTRACT

A system for activating a dental handpiece connected to a supply hose after removal of the handpiece from a holder is provided. The handpiece includes a circuit with a switch element that acquires a change of an electrical or magnetic field or that can be influenced by such a field when the handpiece is taken from a holder or, respectively, is returned into a holder. The switch element is allocated to the end part of the supply hose facing toward the handpiece; the part that changes or, respectively, influences the field is disposed at the holder.

17 Claims, 3 Drawing Sheets

SYSTEM ACTIVATING A DENTAL HANDPIECE AFTER REMOVAL FROM A HOLDER

FIELD OF THE INVENTION

The present invention relates generally to dental apparatuses and, more specifically, to dental apparatuses which include a plurality of handpieces, each of which are connected to supply hoses and each of which rest upon a holder or deposit device. Still more specifically, the present invention relates to a system for activating a dental handpiece when it is removed from a holder and for deactivating a dental handpiece when it is replaced on a holder.

BACKGROUND OF THE INVENTION

In dental technology, it is known to preselect or activate the handpieces or, respectively, the supply agents thereof upon detachment of the handpieces from their respective deposit devices or holders. To this end, correspondingly fashioned switch elements are located in or at the holder with one switch being provided for each handpiece. The switch elements can be microswitches, light barriers or inductive sensors as well as shown in EP-0 005 791-B1.

It is a disadvantage that a switch element for each handpiece must be present at practically every holder. Since the holders are usually designed as claw-shaped receiving elements in the form of an open ring, it is necessary, for example, given arrangement of a light barrier, to provide a transmitter and a receiver for each side of the opening. Given the standard practice of equipping of a dental apparatus with at least four through six handpieces, this means that the plurality of light barriers corresponding to each handpiece must be provided even when fewer handpieces are used or, respectively, desired by the physician or dentist.

Further disadvantages include the possibility of disturbances at the transmitter or receiver due to environmental or other influences. With light barriers, for example, disturbances can arise due to the incidence of extraneous light or due to contaminants. Embodiments with mechanical switch elements are also not free of disturbances. For example, the adjustment can be modified or worn due to frequent switching, so that the switch elements no longer work in a reliable manner.

A further, critical disadvantage given the known embodiments is that a deposit of a handpiece at a different location, for example at an interim deposit of a tray, is not possible or is only possible on the basis of additional, manual switching events.

SUMMARY OF THE INVENTION

The invention is based on the object of creating a means for recognizing the removal of a handpiece connected to a supply hose from a holder where the aforementioned disadvantages can be avoided. In particular, an object is to enable a sure recognition of a removed or employed handpiece, namely independently of where the handpiece was previously deposited or held.

A switch element is inventively provided that acquires a change of an electrical or magnetic field or can be influenced by such a field when the handpiece is taken from a holder or, respectively, is returned to a holder, in that the switch element is arranged at that end of the supply hose facing toward the handpiece and the part that modifies or, respectively, influences the field is allocated to the holder and not the handpiece, and therefore the holder and any arbitrary deposit device can be utilized for any instrument or handpiece. Therefore, neither a holder with adjusted switch elements quite specifically matched to a specific handpiece need be provided nor does the handpiece itself have to be fashioned with reference to the recognition of the removal of the handpiece. This aspect is significant insofar as the handpieces must be changed more frequently than the corresponding supply hoses.

The switch element to be arranged in the supply hose at the hose coupling of the handpiece side can be a small reed switch, an inductive coil or a capacitative receiver as well. Only either a magnetic or non-magnetic metallic part need be arranged at the holder itself. Due to metal part or magnet part—which the physician or dentist can potentially introduce into the holder—the handpiece reports whether it lies in the holder or is removed therefrom. The holders can be arranged at an arbitrary location; they therefore need not have a fixed allocation to a handpiece. An ergonomically more beneficial working can thereby be achieved. A more cost-beneficial manufacture of the overall dental apparatus is likewise possible.

Particular advantages are to be seen therein that what is referred to as a fast or interim holder for handpieces can be provided at an arbitrary location of a dental work station. A further advantage is to be seen therein that no electrical, pneumatic or other leads need be conducted to the deposit devices.

In an embodiment, the system of the present invention includes a handpiece connected to an end of a supply hose. The handpiece also removably engages a holder. The system further includes a circuit that includes a switch element that is switched upon the modification of a field consisting of an electric field or a magnetic field when the handpiece is either removed from the holder or returned to the holder.

In an embodiment, the switch element is disposed in the end of the supply hose that is connected to the handpiece.

In an embodiment, the modification of the field occurs when a distance between the switch element and a field-modifying part changes as the handpiece is either removed from or returned to the holder.

In an embodiment, the switch element is a read switch and the field-modifying part is a permanent magnet.

In an embodiment, the switch element is a magnetic coil and the field-modifying part is a metallic part.

In an embodiment, the system comprises a plurality of handpieces, each of which are connected to a supply hose and a plurality of holders. A switch element is disposed between each supply hose and its respective handpiece. The handpieces are not assigned to any single holder so that removal of a handpiece from any one of the holders results in a closing of the switch and an activation of the handpiece and return of the handpiece to any one of the holders results in an opening of the switch and a deactivation of the handpiece.

It is therefore an advantage of the present invention to provide a dental workstation with a plurality of handpieces and a plurality of handpiece holders whereby a handpiece is activated upon removal of the handpiece from any one of the holders and deactivated upon return of the handpiece to any one of the holders.

Another advantage of the present invention is to provide a dental workstation whereby the handpieces are not assigned to any one specific holder but may be returned or stored on any available holder.

Another advantage of the present invention is to provide an improved system for activating and deactivating dental handpieces.

Other objects and advantages of the present invention will become apparent upon reading the following detailed description and appended claims, and upon reference to the accompanying drawings.

BRIEF DESCRIPTION OF THE DRAWINGS

Two exemplary embodiments of the invention are described in greater detail below and shown in the following drawings wherein.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

Figure 1:
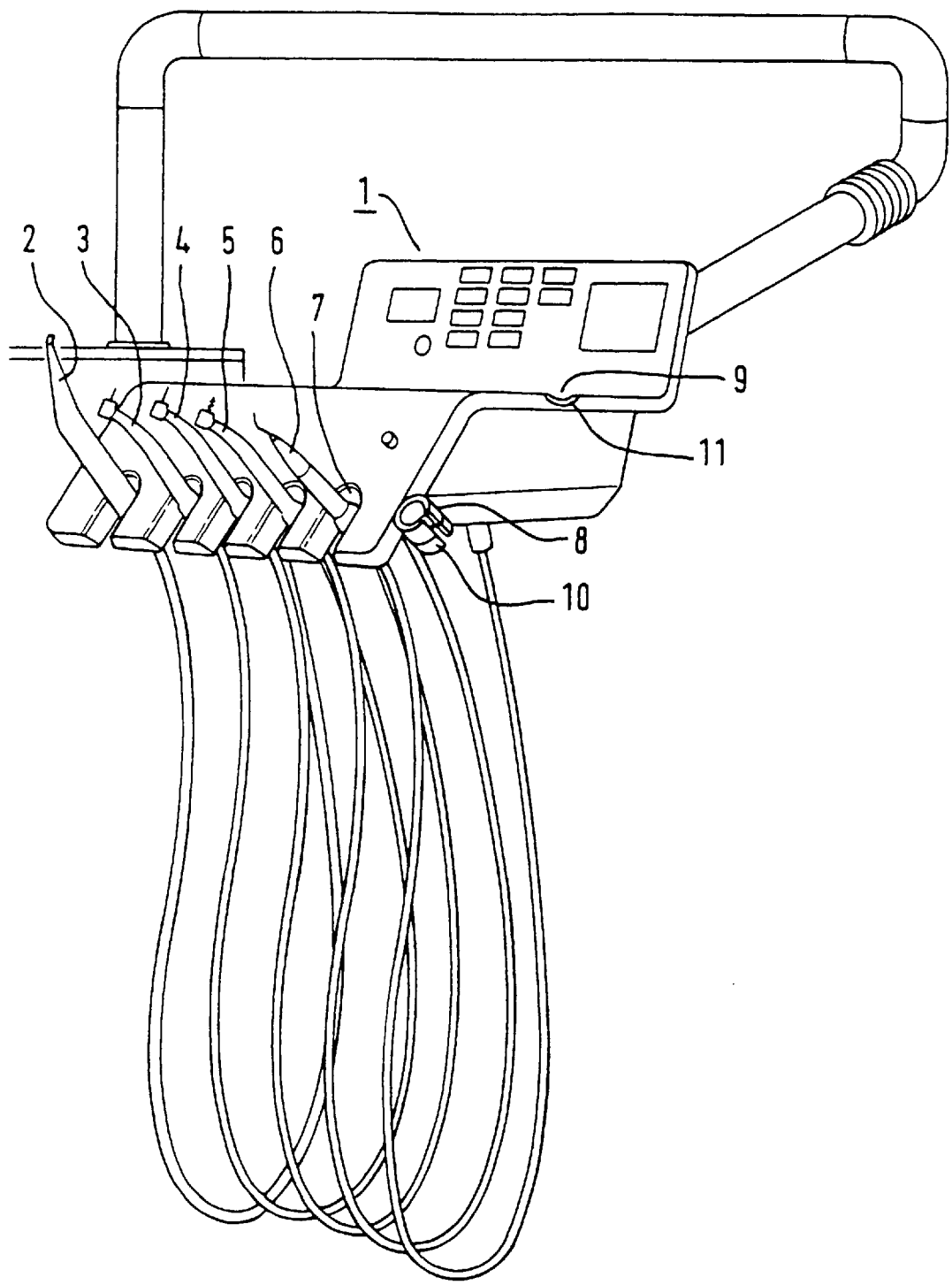
FIG. 1 is a perspective view of a dental work apparatus with a plurality of handpieces and a plurality of holders.

In a schematic illustration, FIG. 1 illustrates a portion of a dental work station with a treatment apparatus 1 that contains a plurality of handpieces 2 through 6. The handpieces 2 through 6 are differently designed and also have different functions. The handpiece 2 is a spray handpiece; the handpieces 3 through 5 are drill handpieces; the handpiece 6 is a plaque removal handpiece. The deposit devices of holders allocated to the handpieces 2 through 6 are referenced 7.

In addition to these deposit devices, the treatment apparatus 1 contains two further holders 8 and 9 that serve for the interim deposit of one of the handpieces 2 through 6. Whereas the holder 8 is constructed similar to the holders 7, the holder 9 is fashioned as a horizontal deposit depression or groove.

Figure 2:
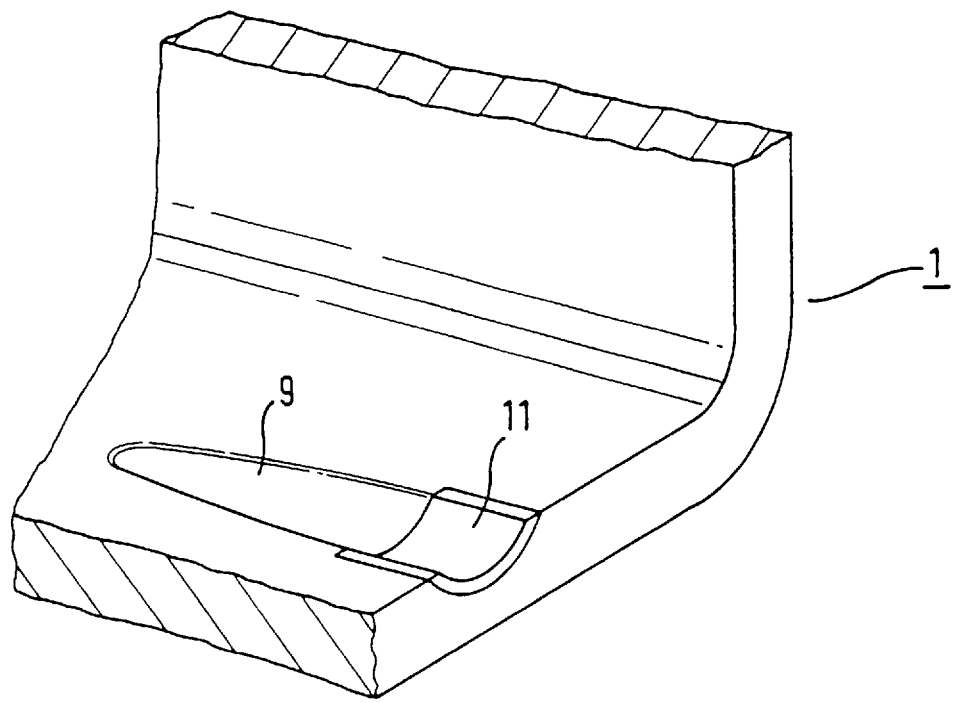
FIG. 2 is a partial view of the work apparatus shown in FIG. 1.

FIG. 2 illustrates a magnified view of this deposit depression.

At their ends facing toward the supply hoses, the holders 7 through 9 contain an insert or attachment part 10 or 11 that collaborates with a switch element arranged in the connector part of the supply hose at the handpiece side, as shall be explained later. The insert/attachment part 10, 11 can be a permanent magnet or a metallic part dependent on which switch element is employed in the connector part of the supply hose. Advantageously, the parts are mounted interchangeably. At the holder 9, this can be a removable half-shell; at the holders 7 and 8, the insert/attachment parts 10 can be an open ring that, adapted to the holder, is attached at the underside thereof.

Figure 3:
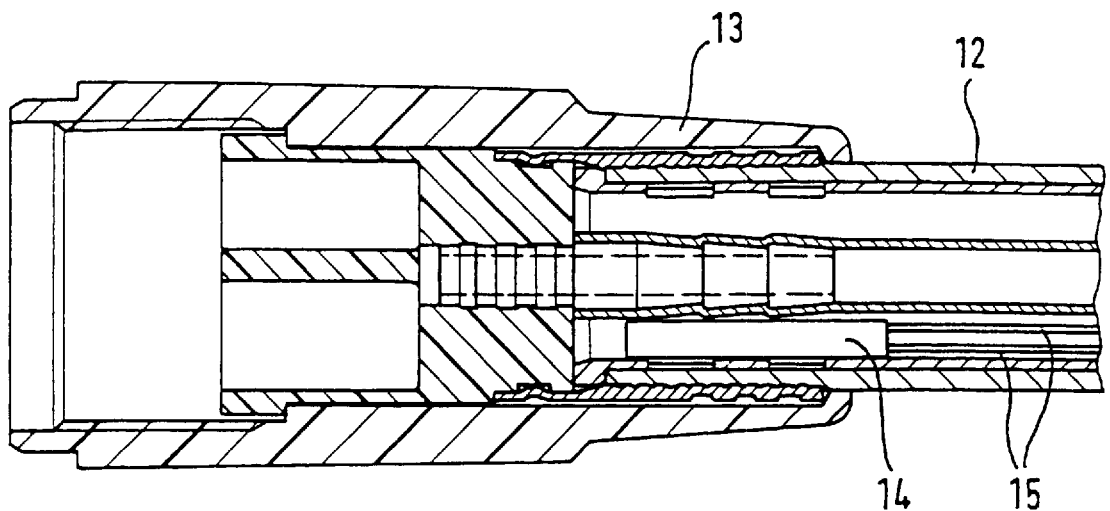
FIG. 3 is a sectional view of a first embodiment of a switch element at the hose fitting of the handpiece side.

In a longitudinal section, FIG. 3 shows the end section at the handpiece side of a supply hose 12 with a connection fitting 13 for the connection of one of the handpieces 2 through 6. Other than the connections (not referenced in detail) for the agent lines, the connection fitting contains a reed switch 14 that is connected according to the block circuit diagram of FIG. 4. The reed switch 14 interacts with a permanent magnet that is arranged the holders 7 through 9 in the aforementioned way as attachment part 10 or insert part 11. The reed switch 14 responds when a handpiece is taken from the holder or, respectively, is placed back into the holder.

Figure 4:
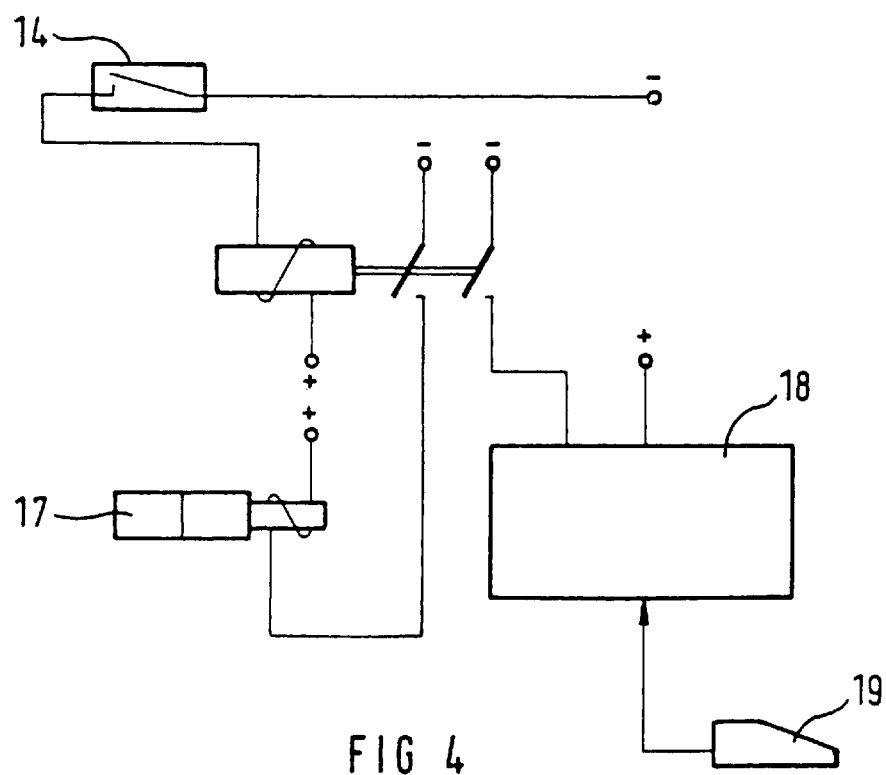
FIG. 4 is a schematic diagram of the embodiment shown in FIG. 3.

When viewing FIG. 4, which shows a block circuit diagram with such a reed switch, it can be seen that the contact of the reed switch 14 is open. This switch position corresponds to the deposited condition. When a handpiece is taken from the deposit mechanism or holder, the contact is closed and, thus, a relay is switched, as a result whereof a pre-selection solenoid 17 for the control of the flow of the agents of air and/or water is enabled from a power electronics 18. The enabling can ensue via a foot switch 19 in a known way.

For example, a line rupture can be monitored in that the reed switch 14 is open in the deposited condition of a handpiece but closed in the removed condition. Moreover, this type of switch has the advantage that the outputs are closed when no handpiece is connected to the hose coupling.

Figure 5:
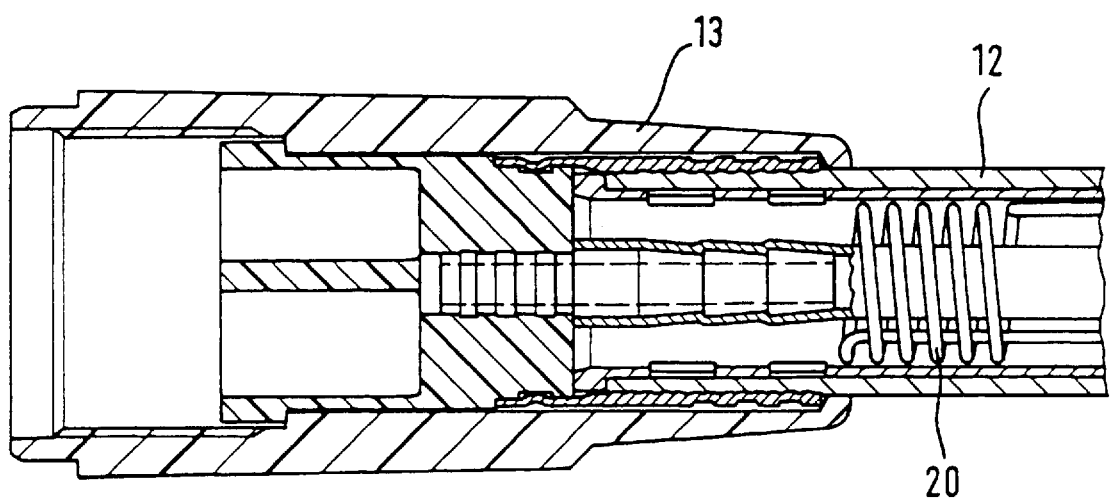
FIG. 5 is a sectional view of a second embodiment of a switch element at the hose fitting of the handpiece side.

FIG. 5 shows a second variation of an embodiment with a magnetic coil 20 that forms a resonant circuit that is detuned by a metallic part in the holders. First, the removal of the handpiece can be recognized with this field influencing, and a switch signal can then be output to a pre-selection solenoid for the control of the agent flow in the above-described way.

From the above description, it is apparent that the objects and advantages of the present invention have been achieved. While only certain embodiments have been set forth, alternative embodiments and various modifications will be apparent from the above description to those skilled in the art. These and other alternatives are considered equivalents and within the spirit and scope of the present invention.

What is claimed:

1. A system for recognizing a removal of a dental handpiece from a holder, the system comprising:

a handpiece connected to an end of a supply hose, the handpiece removably engaging a holder, the system further comprising a circuit comprising a switch element that is switched upon a modification of a field selected from the group consisting of an electrical field and a magnetic field, the field being modified when a distance between the switch element and a field-modifying part changes when the handpiece is removed from or returned to the holder, the switch element being disposed in the end the supply hose that is connected to the handpiece, the field-modifying part being connected to the holder.

2. The system of claim 1 wherein the switch element is disposed inside a connection fitting disposed between the end of the supply hose and the handpiece.

3. The system of claim 1 wherein the switch element is a reed switch, the field-modifying part is a permanent magnet.

4. The system of claim 3 wherein the reed switch is connected to a relay, the reed switch being open when the handpiece is resting on the holder.

5. The system of claim 1 wherein the circuit is a resonant circuit, the switch element is a magnetic coil, the field-modifying part is a metallic part.

6. A system for activating a dental handpiece upon removal of the handpiece from a holder and for deactivating the dental handpiece when the handpiece is returned to the holder, the system comprising:

a handpiece being connected to an end of a supply hose, the handpiece removably engaging a holder, the holder comprising a field-modifying part, the system further comprising a switch element disposed at a connection between the handpiece and the supply hose, the switch element being switched to a closed position and the handpiece being activated when a distance between the switch element and the field-modifying part increases as the handpiece is removed from the holder, the switch element being switched to an open position and the handpiece being deactivated when the handpiece is returned to the holder.

7. The system of claim 6 wherein the switch element is disposed inside a connection fitting disposed between the end of the supply hose and the handpiece.

8. The system of claim 6 wherein the switch element is a reed switch, the field-modifying part is a permanent magnet.

9. The system of claim 1 wherein the switch element is a magnetic coil, the field-modifying part is a metallic part. and each of the metallic parts is a magnet.

10. A system for activating a dental handpiece upon removal of one of the handpieces from one of a plurality of handpiece holders and for deactivating the dental handpiece when the handpiece is returned to one of the holders, the system comprising:

a plurality of handpieces, a plurality of supply hoses and a plurality of holders, each of the handpieces being connected to an end of one of the supply hoses at a connection, each of the handpieces removably engaging one of the holders, each of the holders comprising a metallic part, each connection of each comprising a switch element, each of the switch elements being switched to a closed position thereby activating the handpiece connected thereto when the handpiece connected thereto is removed from any one of the holders, each of the switch elements being switched to an open position thereby deactivating the handpiece connected thereto when the handpiece connected thereto is returned to any one of the holders.

11. The system of claim 10 wherein each of the switch elements is a reed switch and each of the metallic parts is a magnet.

12. The system of claim 10 wherein each of the switch elements is a magnetic coil.

13. A system for recognizing a removal of a dental handpiece from a holder, the system comprising:

a handpiece connected to an end of a supply hose, the handpiece removably engaging a holder, the system further comprising a circuit comprising a switch element that is switched upon a modification of a field selected from the group consisting of an electrical field and a magnetic field, the field being modified when a distance between the switch element and a field-modifying part changes when the handpiece is removed from or returned to the holder, the switch element being disposed in the end the supply hose that is connected to the handpiece, the field-modifying part being connected to the holder, the circuit being a resonant circuit, the switch element being a magnetic coil, the field-modifying part being a metallic part.

14. The system of claim 13 wherein the switch element is disposed inside a connection fitting disposed between the end of the supply hose and the handpiece.

15. A system for activating a dental handpiece upon removal of the handpiece from a holder and for deactivating the dental handpiece when the handpiece is returned to the holder, the system comprising:

a handpiece being connected to an end of a supply hose, the handpiece removably engaging a holder, the holder comprising a field-modifying part, the system further comprising a switch element disposed at a connection between the handpiece and the supply hose, the switch element being switched to a closed position and the handpiece being activated when a distance between the switch element and the field-modifying part increases as the handpiece is removed from the holder, the switch element being switched to an open position and the handpiece being deactivated when the handpiece is returned to the holder, the switch element being a magnetic coil, the field-modifying part being a metallic part.

16. The system of claim 15 wherein the switch element is disposed inside a connection fitting disposed between the end of the supply hose and the handpiece.

17. A system for activating a dental handpiece upon removal of one of the handpieces from one of a plurality of handpiece holders and for deactivating the dental handpiece when the handpiece is returned to one of the holders, the system comprising:

a plurality of handpieces, a plurality of supply hoses and a plurality of holders, each of the handpieces being connected to an end of one of the supply hoses at a connection, each of the handpieces removably engaging one of the holders, each of the holders comprising a metallic part, each connection of each comprising a switch element, each of the switch elements being switched to a closed position thereby activating the handpiece connected thereto when the handpiece connected thereto is removed from any one of the holders, each of the switch elements being switched to an open position thereby deactivating the handpiece connected thereto when the handpiece connected thereto is returned to any one of the holders, each of the switch elements being a magnetic coil.

* * * * *